United States Patent [19]

Bergstrom et al.

[11] Patent Number: 4,539,293

[45] Date of Patent: Sep. 3, 1985

[54] PRODUCTION OF BUTANOL BY FERMENTATION IN THE PRESENCE OF COCULTURES OF CLOSTRIDIUM

[75] Inventors: Sheryl L. Bergstrom, Duarte, Calif.; Gary L. Foutch, Stillwater, Okla.

[73] Assignee: The United states of America as represented by the Administrator of the National Aeronautics and Space Administration, Washington, D.C.

[21] Appl. No.: 493,179

[22] Filed: May 10, 1983

[51] Int. Cl.³ .......................... C12P 7/16; C12R 1/145
[52] U.S. Cl. ..................................... 435/160; 435/842
[58] Field of Search .................. 435/41, 42, 150, 155, 435/160, 161, 162, 813, 820, 842

[56] References Cited

U.S. PATENT DOCUMENTS 4,400,470 8/1983 Zeikus et al. .................. 435/162
4,424,275 1/1984 Levy ................................. 435/160

*Primary Examiner*—Sidney Marantz
*Assistant Examiner*—C. Lee Foulke
*Attorney, Agent, or Firm*—Paul F. McCaul; John R. Manning; Thomas H. Jones

[57] ABSTRACT

Sugars are converted to a mixture of solvents including butanol by a fermentation process employing a coculture of microorganisms of the Clostridium genus, one of said microorganisms favoring the production of butyric acid and the other of which converts the butyric acid so produced to butanol. The use of a coculture substantially increases the yield of butanol over that obtained using a culture employing only one microorganism.

4 Claims, No Drawings

PRODUCTION OF BUTANOL BY FERMENTATION IN THE PRESENCE OF COCULTURES OF CLOSTRIDIUM

BACKGROUND OF THE INVENTION

Origin of the Invention

The invention described herein was made in the performance of work under a NASA Contract and is subject to the provisions of Section 305 of the National Aeronautics and Space Act of 1958, Public Law 85-568 (72 STAT 435; 43 USC 2457).

Field of the Invention

This invention relates to the production of butanol by fermentation of sugars in the presence of two different microorganisms of the Clostridium genus.

Background Discussion

Butanol may be produced by the fermentation of carbohydrates which break down into sugars, for example, sugars containing five and six carbon atoms such as glucose. This process was developed by Dr. Charles Weizmann during World War I and was the principal source of butanol until this chemical was produced from low-priced hydrocarbon feedstocks. To a large extent this process has been replaced, but it is still used on a commercial scale in the Union of South Africa. Nevertheless, with the increasing cost of hydrocarbon feedstocks plus the possible additional uses of butanol in, for example, oil field tertiary recovery processes, the demand for butanol is increasing and the Weizmann Process now has potential commercial application in the United States.

Briefly, the Weizmann Process comprises fermenting a suitable feedstock such as molasses sugars in the presence of Clostridium microorganisms which convert the sugar to a solvent mixture of butanol, acetone and ethanol. Typically, from 29 to 33 weight percent of the fermentable carbohydrates are converted to these solvents. In the solvent mixture the usual ratio of butanol to acetone to ethanol is approximately 6:3:1. The process is a batch process as opposed to a continuous process, and, when fermentation is completed, the solvent mixture is separated from the spent materials.

SUMMARY OF THE INVENTION

We have discovered that the yield of butanol from the Weizmann Process may be substantially increased, for example, by as much as 20% or even more, by using a coculture of at least two different Clostridium species. One of these species should favor the production of butyric acid and the other species should favor the conversion of this butyric acid to butanol. The two different species could be used concurrently in the same reaction vessel or in a multiple stage system wherein (1) the species which favors the production of butyric acid is in a first stage and acts on the feedstock to convert the fermentable carbohydrates to butyric acid and (2) in a second stage products from the first stage are fed into a second reaction vessel wherein the second species acts on the butyric acid to convert it to butanol. At equilibrium in the single stage system, the number ratio of the butyric acid forming species to butanol conversion species should range between about 1:3 and about 3:1.

Although several species may be employed, we have found that *Clostridium pasteurianum* is particularly suited to form the butyric acid. Also, but to a lesser degree, the species *Clostridium butyricum* is also useful in forming the butyric acid. Two different species of the second microorganism which converts the butyric acid to butanol have been employed. The most preferred is *Clostridium butylicum*. In the preferred mode of practicing this invention, a coculture of the *C. pasteurianum* and *C. butylicum* species is employed in a single stage reactor to convert the feedstock to butanol, acetone and ethanol. *Clostridium acetobutylicum* may also be used in place of, or concurrently with, the *C. butylicum* species.

In accordance with the most preferred way of practicing the invention, a coculture of the *C. pasteurianum* and *C. butylicum* species are mixed with glucose as the feedstock in the presence of a suitable nutrient and allowed to ferment until gas production terminates. Preferably, the mixture is buffered so that the pH of the reaction mixture remains in the range of from about 4.5 to about 5.2. The most preferred temperature for incubation of the reaction mixture is about 37° C. This temperature permits the microorganisms to be most active.

The amount of butanol produced by the process of this invention was compared with the amount of butanol produced by conventional processes. Results indicated that the process of this invention yielded an increase of at least 20%, which is very significant and represents a substantial economic benefit. For example, the solvent mixture of butanol, acetone, and ethanol usually has, at a maximum, 60 weight percent butanol. With the process of this invention, the percentage of butanol is typically 70 weight percent or more in the solvent mixture.

EXAMPLES

The following presents experimental results using the cocultures of this invention to produce butanol by the Weizmann Process. The results of these experiments are set forth in Tables 1 and 2. Both tables present test data based on conducting the Weizmann Process using cocultures and single microorganism systems. Table 1 presents data in which the reaction mixture was buffered with calcium carbonate. Table 2 presents data in which the reaction mixture was not buffered. Buffering is highly desirable in order to maintain the pH of the reaction mixture in the desired range. If the pH of the reaction mixture is outside of this range, the yield of butanol is substantially reduced.

The fermentation process was conducted using conventional procedures, with the exception that cocultures were employed in accordance with the principle of this invention. The cocultures were grown and maintained on Cooked Meat Media provided by the Baltimore Biological Laboratories and identified as No. 11128. This media was maintained in Brewer jars under anaerobic conditions. After an initial growth of approximately 48 hours, the cultures were transferred to 30 milliliter serum bottles containing Thioglycollate Medium without added dextrose. Two and one-half weight percent glucose was added to the Thyioglycollate media without dextrose. Also, a chip of calcium carbonate was added for the purpose of preventing a decrease in pH. The cultures were incubated at 37° C., with the sample being ventilated daily to prevent buildup of gas. Correct conditions were maintained so that the microorganisms grew under anaerobic conditions. The following lists the microorganisms tested, which were supplied by the Northern Regional Research Center of the Department of Agriculture in Peoria, Illinois.

| MICROORGANISM TESTED | |
| --- | --- |
| | Strain No. |
| 1. Clostridium pasteurianum | NRRL B598 |
| 2. Clostridium butyricum | NRRL B1092 |
| 3. Clostridium butylicum | NRRL B592 and NRRL B593 |
| 4. Clostridium acetobutylicum | NRRL B527 |

Gas chromatography analytical procedures were employed to determine the quantities of ethanol, acetone, acetic acid, butyric acid, and butanol produced. A Hewlett Packard Model 5880A was used, employing Porapak QS as the absorbent medium in a 5-foot×⅛-inch diameter stainless steel column. The total sugars were analyzed using dinitrosalicylate reagent supplied by Kodak Chemical Company. The following Tables 1 and 2 present the test data obtained.

TABLE 1

| | (With Buffer) Weight percent | | | | |
| --- | --- | --- | --- | --- | --- |
| STRAIN | ETH-ANOL | ACE-TONE | ACETIC ACID | BUTA-NOL | BUTYRIC ACID |
| NRRL B593 | 0.01 | 0.26 | neg. | 0.45 | 0.24 |
| NRRL B598 | neg.* | neg. | 0.23 | neg. | 0.63 |
| NRRL B593 and B598 | 0.03 | 0.32 | neg. | 0.54 | 0.17 |
| NRRL B592 | 0.05 | 0.16 | 0.28 | 0.46 | 0.13 |
| NRRL B598 | neg. | neg. | 0.23 | neg. | 0.63 |
| NRRL B592 and B598 | 0.06 | 0.20 | 0.35 | 0.70 | 0.16 |

*neg - none detected

TABLE 2

| | (Without Buffer) | | | | |
| --- | --- | --- | --- | --- | --- |
| STRAIN | ETH-ANOL | ACE-TONE | ACETIC ACID | BUTA-NOL | BUTYRIC ACID |
| NRRL B593 | 0.03 | 0.09 | 0.25 | 0.40 | 0.20 |
| NRRL B598 | neg.* | neg. | 0.12 | neg. | 0.55 |
| NRRL B593 | 0.02 | 0.11 | 0.24 | 0.47 | 0.13 |

TABLE 2-continued

| | (Without Buffer) | | | | |
| --- | --- | --- | --- | --- | --- |
| STRAIN | ETH-ANOL | ACE-TONE | ACETIC ACID | BUTA-NOL | BUTYRIC ACID |
| and B598 | | | | | |

*neg: none detected

The test results, particularly Column 5, substantiates that the amount of butanol produced is substantially increased by employing a coculture is accordance with the teachings of this invention. By the proper selection of cocultures, the yield of butanol can be substantially increased over what is conventionally obtained.

The above description presents the best mode contemplated of carrying out the present invention. This invention is, however, susceptible to modifications from the embodiments discussed in the above examples. Consequently, it is not the intention to limit this invention to the particular examples disclosed. On the contrary, the intention is to cover all modifications falling within the spirit and scope of the invention as expressed in the appended claims.

What is claimed is:

1. A process for the production of butanol from sugar comprising the steps of:

mixing sugar with a coculture of a species of *Clostridium pasteurianum* and a species of *Clostridium butylicum;* fermenting the sugar with the coculture to produce an organic solvent mixture containing butanol in which the amount of butanol is increased by at least 20 percent as compared to a fermentation process using *Clostridium butylicum,* and recovering the butanol.

2. The process of claim 1 wherein a solvent mixture of butanol, acetone and ethanol is produced by the coculture cultivation and said solvent mixture contains at least approximately 70 weight percent butanol.

3. The process of claim 1 wherein the pH of the coculture is maintained in the range of from about 4.5 to about 5.2.

4. The process of claim 1 wherein the process is conducted in a single stage system in which, at equilibrium, the weight ratio of *Clostridium pasteurianum* to *Clostridium butylicum* ranges between about 1:3 and about 3:1.

* * * * *